(12) United States Patent
Seo

(10) Patent No.: US 11,422,103 B1
(45) Date of Patent: Aug. 23, 2022

(54) METHOD AND SYSTEM FOR DETECTING CONCENTRATION OF ANALYTE BASED ON OSCILLATOR HAVING SELECTIVE FREQUENCY CHARACTERISTIC

(71) Applicant: SB Solutions Inc., Ulsan (KR)

(72) Inventor: Seungup Seo, Ulsan (KR)

(73) Assignee: SB SOLUTIONS INC., Ulsan (KR)

( * ) Notice: Subject to any disclaimer, the term of this patent is extended or adjusted under 35 U.S.C. 154(b) by 0 days.

(21) Appl. No.: 17/399,938

(22) Filed: Aug. 11, 2021

(30) Foreign Application Priority Data

Jun. 2, 2021 (KR) .......................... 10-2021-0071305

(51) Int. Cl.
*G01N 27/04* (2006.01)
*G01N 27/07* (2006.01)

(52) U.S. Cl.
CPC ........... *G01N 27/045* (2013.01); *G01N 27/07* (2013.01); *G01N 2291/014* (2013.01)

(58) Field of Classification Search
CPC ...... G01N 27/045; G01N 27/07; G01N 27/04; G01N 27/00; G01N 2291/014
See application file for complete search history.

(56) References Cited

U.S. PATENT DOCUMENTS

| 5,811,664 | A | * | 9/1998 | Whittington | ........... | G01V 3/101 |
| | | | | | | 73/53.07 |
| 2004/0194547 | A1 | * | 10/2004 | Tozaki | ................... | G01N 29/11 |
| | | | | | | 73/579 |
| 2008/0135614 | A1 | * | 6/2008 | Werner | .............. | G06K 19/0723 |
| | | | | | | 235/439 |

FOREIGN PATENT DOCUMENTS

KR 10-2185556 B1 12/2020

* cited by examiner

*Primary Examiner* — Suman K Nath
(74) *Attorney, Agent, or Firm* — Christensen O'Connor Johnson Kindness PLLC

(57) ABSTRACT

Disclosed are a method and system for detecting a concentration of an analyte based on an oscillator having a selective frequency characteristic. The method may include generating a fringing field, generating various resonant frequencies by changing a resistance value of a resistor-capacitor (RC) oscillator, measuring a change in each of the various resonant frequencies generated by the RC oscillator based on a change in capacitance attributable to a change in an analyte within a region of the fringing field, and measuring a change characteristic of the analyte within the fringing field based on the change in each of the various resonant frequencies.

17 Claims, 11 Drawing Sheets

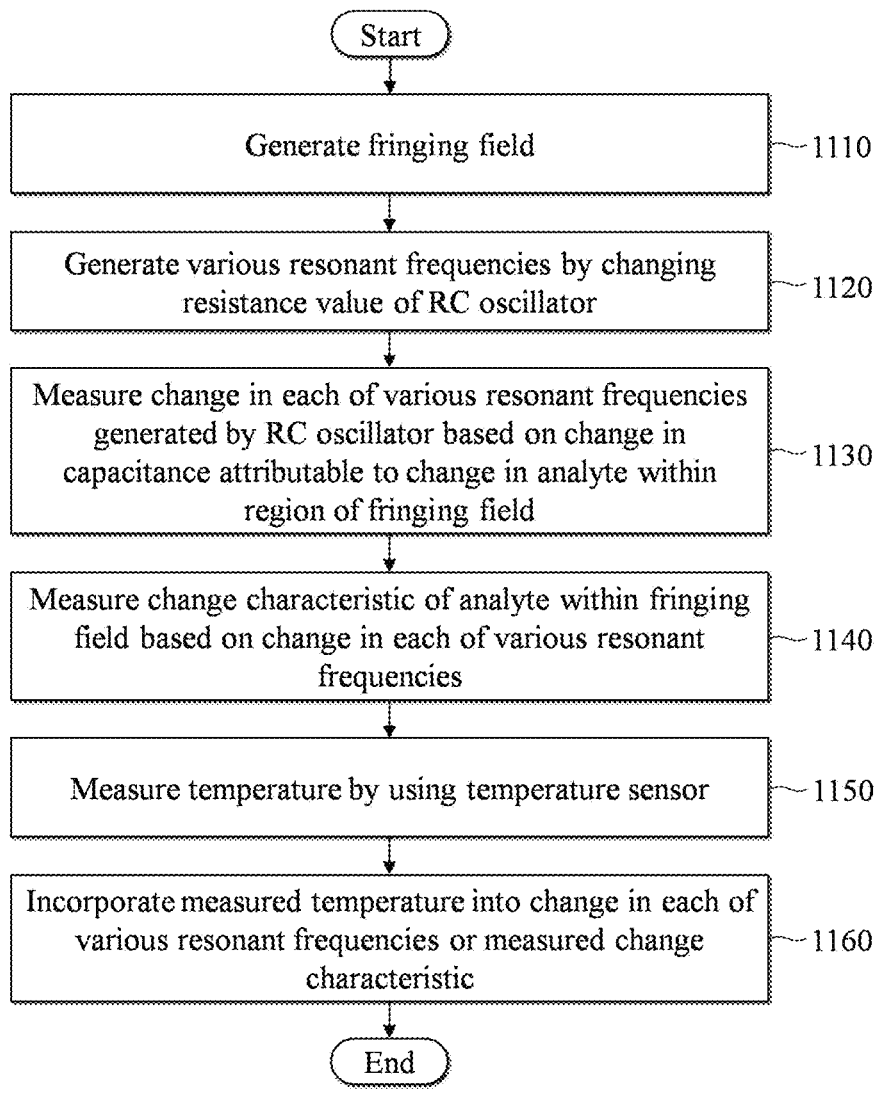

METHOD AND SYSTEM FOR DETECTING CONCENTRATION OF ANALYTE BASED ON OSCILLATOR HAVING SELECTIVE FREQUENCY CHARACTERISTIC

CROSS-REFERENCES TO RELATED APPLICATIONS

This application is based on and claims priority under 35 U.S.C. 119 to Korean Patent Application No. 10-2021-0071305, filed on Jun. 2, 2021, in the Korean intellectual property office, the disclosures of which are herein incorporated by reference in their entireties.

TECHNICAL FIELD

The following description relates to a method and system for detecting a concentration of an analyte based on an oscillator having a selective frequency characteristic.

BACKGROUND OF THE INVENTION

Examples in which adult-onset diseases, such as diabetes, hyperlipidemia and thrombosis, are increased are continuously reported. Such diseases need to be periodically measured using various bio sensors because it is important to continuously monitor and manage the diseases. A common type of bio sensor is a method of injecting, into a test strip, blood drawn from a finger and then quantizing an output signal by using an electrochemical method or a photometry method. Such an approach method causes a user a lot of pain because blood needs to be drawn every time.

For example, in order to manage diabetes of hundreds of millions of people around the globe, the most basic thing is to measure blood glucose. Accordingly, a blood glucose measurement device is an important diagnostic unit essential for a diabetes patient. Various blood glucose measurement devices are recently developed, but the most common method is a method of gathering blood by pricking a patient's finger and directly measuring a concentration of glucose within the blood. An invasive method includes a method of penetrating an invasive sensor into the skin, measuring a concentration of glucose through the invasive sensor for a given time, and measuring blood glucose by recognizing the blood glucose through an external reader.

In contrast, a non-invasive method includes a method using a light-emitting diode (LED)-photo diode (PD). However, the non-invasive method has low accuracy due to environmental elements and foreign substances, such as sweat or a temperature, because the LED-PD is attached to the skin.

The aforementioned information is to merely help understanding, and may include contents which do not form a part of a conventional technology and may not include contents which may be presented to those skilled in the art through a conventional technology.

Prior Art Document Number

Korean Patent No. 10-2185556

SUMMARY

This summary is provided to introduce a selection of concepts in a simplified form that are further described below in the Detailed Description. This summary is not intended to identify key characteristics of the claimed subject matter, nor is it intended to be used as an aid in determining the scope of the claimed subject matter.

The present disclosure provides a method and system for detecting a concentration of an analyte, which can obtain more accurate data of an analyte by obtaining various data into which a concentration of the analyte has been incorporated in a way to form an R-bank capable of variously forming a value of an R component among the R component and a C component that generate a resonant frequency of a resistor-capacitor (RC) oscillator, to generate various resonant frequencies based on the value of the R component selected by the R-bank, and detect and measure a change.

The present disclosure provides a method and system for detecting a concentration of an analyte, wherein various elements, such as a race, gender, an age, and an environment which may change an environment within the body, can be incorporated into a resonant frequency based on a value of an R component selected by an R-bank.

In an aspect, there is provided a method of detecting a concentration of an analyte, including generating a fringing field, generating various resonant frequencies by changing a resistance value of a resistor-capacitor (RC) oscillator, measuring a change in each of the various resonant frequencies generated by the RC oscillator based on a change in capacitance attributable to a change in an analyte within a region of the fringing field, and measuring a change characteristic of the analyte within the fringing field based on the change in each of the various resonant frequencies.

According to an aspect, generating the resonant frequency may include changing the resistance value of the RC oscillator through a resister-bank (R-bank) included in the RC oscillator. The R-bank may be implemented to selectively use one of multiple resistance values or to provide a variable resistance value.

According to another aspect, generating the fringing field may include generating the fringing field by using a fringing field capacitor included in the RC oscillator.

According to yet another aspect, the change in capacitance may be measured based on a change in permittivity by using a material under test (MUT) unit including a material having a dielectric constant.

According to yet another aspect, the method may further include measuring a temperature by using a temperature sensor and incorporating the measured temperature into the change in each of the various resonant frequencies or the measured change characteristic of analyte.

According to yet another aspect, the method may further include obtaining activity information of an object based on an angular speed measured by a gyro sensor, and compensating for the measured change characteristic of analyte based on the obtained activity information of the object.

In an aspect, there is provided a system for detecting a concentration of an analyte, including a sensor unit and a processing unit. The sensor unit may be configured to generate a fringing field, generate various resonant frequencies by changing a resistance value of a resistor-capacitor (RC) oscillator, and generate various resonant frequencies into each of which a change in capacitance attributable to a change in an analyte within a region of the fringing field has been incorporated. The processing unit may be configured to measure a change characteristic of the analyte within the fringing field based on the change in each of the various resonant frequencies into each of which the change in the capacitance has been incorporated.

According to an aspect, the sensor unit may include the RC oscillator configured to generate the fringing field and the various resonant frequencies.

According to another aspect, the RC oscillator may include a fringing field capacitor configured to generate the fringing field, and a resister-bank (R-bank) implemented to selectively use one of multiple resistance values or to provide a variable resistance value.

According to yet another aspect, the sensor unit may change the resistance value of the RC oscillator by using the R-bank included in the RC oscillator.

According to yet another aspect, the fringing field capacitor may include a sensor pattern for generating the fringing field and a material under test (MUT) unit including a material having a dielectric constant and configured to measure a change in capacitance attributable to a change in permittivity.

According to yet another aspect, the sensor unit may further include a band pass filter (BPF) configured to filter out a signal having a frequency out of filter specifications from an output signal of the RC oscillator, a buffer configured to provide matching between an output of the BPF and an input of a counter in order to prevent a signal loss, and the counter configured to count a frequency of a scalation signal as a zero-cross detection circuit for a signal output by the buffer.

According to yet another aspect, the system may further include a temperature sensor configured to measure a temperature around the sensor unit. The processing unit may incorporate the measured temperature into the change in each of the various resonant frequencies or the measured change characteristic of analyte.

According to yet another aspect, the system may further include a communication unit for communication with another external device, an output unit configured to output at least one of a concentration of the analyte calculated based on the change characteristic of the analyte and a warning based on the concentration of the analyte, and a power management unit configured to provide power to at least one of the sensor unit, the processing unit, the communication unit and the output unit. The processing unit may control an operation of at least one of the sensor unit, the communication unit, the output unit and the power management unit.

According to yet another aspect, the power management unit may include at least one of a battery and a component for wireless power transfer. The component may include a circuit and antenna for wireless power transfer.

According to yet another aspect, the system may further include a noise removal unit configured to remove noise from a signal output by the sensor unit.

According to yet another aspect, the system may further include a gyro sensor configured to measure an angular speed of the system for detecting a concentration of an analyte. The measured change characteristic of analyte may be compensated for based on activity information of an object based on the angular speed.

More accurate data of an analyte can be obtained by obtaining various data into which a concentration of the analyte has been incorporated in a way to form the R-bank capable of variously forming a value of an R component among the R component and a C component that generate a resonant frequency of a resistor-capacitor (RC) oscillator, to generate various resonant frequencies based on the value of the R component selected by the R-bank, and detect and measure a change.

Various elements, such as a race, gender, an age, and an environment which may change an environment within the body, can be incorporated into a resonant frequency based on a value of an R component selected by the R-bank.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 11 is a flowchart illustrating an example of a method of detecting a concentration of an analyte according to an embodiment of the present disclosure.

DETAILED DESCRIPTION

Figure 1:
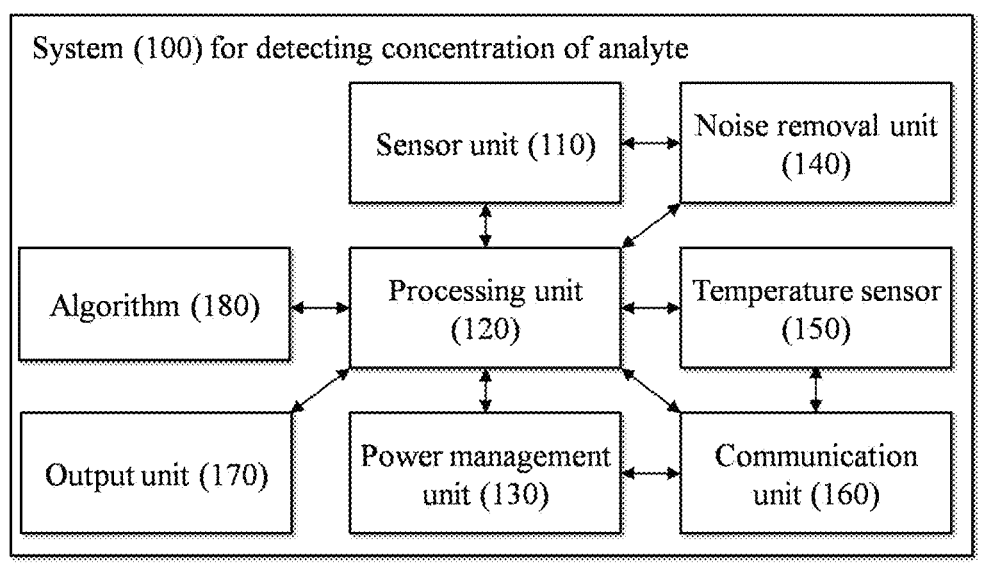
FIG. 1 is a block diagram illustrating an example of internal components of a system for detecting a concentration of an analyte according to an embodiment of the present disclosure.

While illustrative embodiments have been illustrated and described, it will be appreciated that various changes can be made therein without departing from the spirit and scope of the invention.

Hereinafter, embodiments are described in detail with reference to the accompanying drawings. However, the embodiments may be changed in various ways, and the scope of right of this patent application is not limited or restricted by such embodiments. It is to be understood that all changes, equivalents and substitutions of the embodiments are included in the scope of right.

Terms used in embodiments are merely used for a description purpose and should not be interpreted as intending to restrict the present disclosure. An expression of the singular number includes an expression of the plural number unless clearly defined otherwise in the context. In this specification, it should be understood that a term, such as "include" or "have", is intended to designate the presence of a characteristic, a number, a step, an operation, a component, a part or a combination of them described in the specification, and does not exclude the existence or possible addition of one or more other characteristics, numbers, steps, operations, components, parts, or combinations of them in advance.

All terms used herein, including technical or scientific terms, have the same meanings as those commonly understood by a person having ordinary knowledge in the art to which an embodiment pertains, unless defined otherwise in the specification. Terms, such as those commonly used and defined in dictionaries, should be construed as having the same meanings as those in the context of a related technology, and are not construed as being ideal or excessive unless explicitly defined otherwise in the specification.

Furthermore, in describing the present disclosure with reference to the accompanying drawings, the same component is assigned the same reference numeral regardless of its reference numeral, and a redundant description thereof is omitted. In describing an embodiment, a detailed description of a related known art will be omitted if it is deemed to make the gist of the embodiment unnecessarily vague.

Furthermore, in describing components of an embodiments, terms, such as a first, a second, A, B, (a), and (b), may be used. Such terms are used only to distinguish one component from the other component, and the essence, order, or sequence of a corresponding component is not limited by the terms. When it is said that one component is "connected", "combined", or "coupled" to the other component, the one component may be directly connected or coupled to the other component, but it should also be understood that a third component may be "connected", "combined", or "coupled" between the two components.

A component included in any one embodiment and a component including a common function are described using the same name in another embodiment. Unless described otherwise, a description written in any one embodiment may be applied to another embodiment, and a detailed description in a redundant range is omitted.

A system for detecting a concentration of an analyte according to an embodiment may give a warning to a user as an emergency alarm when a value of a biological component predicted by an algorithm based on an immediately measured value or a measured value is greater than a risk level of the biological component.

Such a system for detecting a concentration of an analyte may be implemented in a smart watch type or an embedded type, but the present disclosure is not limited thereto. For example, the system for detecting a concentration of an analyte may be implemented in the form of an implant device inserted into the body of an object. The smart watch type may have a structure including a sensor and a measurement circuit closely attached to a body around the wrist. The embedded type has a structure including a measurement circuit, and a sensor within a band may be placed in an upper arm. In some embodiments, the sensor may be inserted into one or both sides of the band.

FIG. 1 is a block diagram illustrating an example of internal components of a system for detecting a concentration of an analyte according to an embodiment of the present disclosure. The system 100 for detecting a concentration of an analyte according to the present disclosure may include a sensor unit 110, a processing unit 120, a power management unit 130, a noise removal unit 140, a temperature sensor 150, a communication unit 160 and an output unit 170 as hardware devices. Furthermore, the system 100 for detecting a concentration of an analyte may further include an algorithm 180 which may be used to process data measured by the sensor unit 110.

In this case, the output of the sensor unit 110 may correspond to a concentration of one or more analytes present within a bio sample. A fringing field from the sensor unit 110 may be used to detect a fine change in a bio permittivity level attributable to the presence of one or more analytes. The sensor unit 110 may incorporate a change in the permittivity level into a change in the oscillation frequency. As a more detailed example, a sensor may measure a change in the resonant frequency generated by an oscillator based on a change in capacitance attributable to a change in an analyte within a region of the fringing field, and may detect a concentration of the analyte by measuring a change characteristic of the analyte within the fringing field (or a change in the concentration) based on a change in the resonant frequency.

The fringing field may be formed by an electromagnetic force line between two conductors when a voltage is biased to a capacitor, for example. Such a fringing field is more specifically described later with reference to FIG. 5.

In order to generate a fringing field, a resistor-capacitor (RC) oscillator may be used, but the existing RC oscillator has limitations to the use of a limited frequency. In order to solve such a problem, in embodiments of the present disclosure, a resister-bank (R-bank) capable of variously forming a value of an R component among the R component and a C component that generate a resonant frequency of the RC oscillator may be used. The R-bank is more specifically described with reference to FIG. 2.

As a more detailed example, the sensor unit 110 may generate a fringing field and generate various resonant frequencies by changing a resistance value of the RC oscillator, but may generate various resonant frequencies into each of which a change in capacitance attributable to a change in an analyte within a region of the fringing field has been incorporated. To this end, the sensor unit 110 may include the RC oscillator for generating the fringing field and the various resonant frequencies. The RC oscillator may include a fringing field capacitor for generating the fringing field and the R-bank implemented to selectively use one of multiple resistance values or to provide a variable resistance value. In this case, the sensor unit 110 may change a resistance value of the RC oscillator through the R-bank included in the RC oscillator. For example, the sensor unit 110 may change a resistance value of the RC oscillator by using the R-bank under the control of the processing unit 120. In this case, the processing unit 120 may measure a change characteristic in the analyte within the fringing field in response to a change in each of the various resonant frequencies into each of which a change in capacitance has been incorporated.

The processing unit 120 may include a micro controller unit (MCU), and may control operations of the sensor unit 110, the noise removal unit 140, the temperature sensor 150, the communication unit 160 and/or the output unit 170. For example, the processing unit 120 may control operations of the sensor unit 110, the noise removal unit 140, the temperature sensor 150, the communication unit 160 and/or the output unit 170 according to the algorithm 160.

The power management unit 130 may provide power to the sensor unit 110, the processing unit 120, the noise removal unit 140, the temperature sensor 150, the communication unit 150 and/or the output unit 170. The power management unit 130 may include a battery and/or a circuit and antenna for wireless power transmission.

The noise removal unit 140 may be implemented to remove noise from a signal output by the sensor unit 110. For example, the noise removal unit 140 may be implemented to remove high frequency noise. For another example, since a capacitance value may vary due to a heartbeat, the noise removal unit 140 may be implemented to calibrate noise attributable to the heart beat.

The temperature sensor 150 may be implemented to measure a temperature around the system 100 for detecting a concentration of an analyte. The temperature may also affect a biological permittivity level. The processing unit 120 may determine an oscillation frequency of the oscillator attributable to a biological permittivity level based on the original sensor frequency outputted by the sensor unit 110 and temperature data outputted by the temperature sensor 150. For example, the processing unit 120 may calibrate an original sensor frequency outputted by the sensor unit 110 based on a temperature, and may calculate a rate of change in an analyte level in sensing data (i.e., a change in the oscillation frequency (or resonant frequency) based on a change in capacitance) measured based on the calibrated original sensor frequency. Substantially, the processing unit 120 may determine a change or a rate of change in an analyte by incorporating a temperature, measured by the temperature sensor 150, into a change in the resonant frequency or a change characteristic measured with respect to the analyte.

The communication unit 160 may include a wired and/or wireless communication device for enabling the system 100 for detecting a concentration of an analyte to communicate with another device. Communication between the system 100 for detecting a concentration of an analyte and another device through the communication unit 160 may be performed using near field communication (NFC), Bluetooth low energy (BLE), WiFi and/or a 5-th generation mobile communication technology (5G), but the present disclosure is not limited thereto.

The output unit 170 may output a visual, auditory and/or tactile signal to the outside of the system 100 for detecting a concentration of an analyte. For example, the output unit 170 may include a light-emitting diode (LED), a beeper and/or a vibrator in order to provide a user with a warning based on an analyte level. In some embodiments, the output unit 170 may include a digital display device for displaying a measured analyte level.

As described above in brief, the sensor unit 110 may include the RC oscillator used to generate a periodic oscillation signal in an electronic circuit. The oscillator may generate a periodic waveform by only DC power supply. An output waveform may have a square wave, a sine wave or a non-sine wave depending on the type of oscillator.

Figure 2:
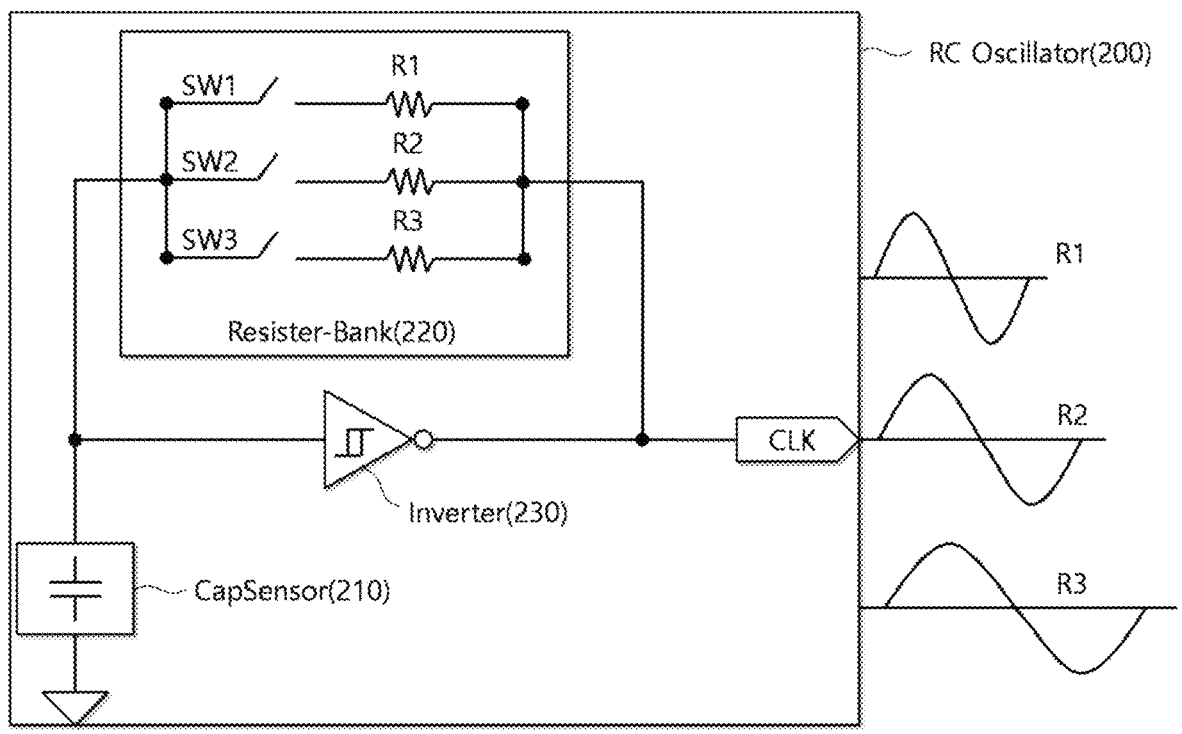
FIG. 2 is a diagram illustrating an example of an RC oscillator according to an embodiment of the present disclosure.

FIG. 2 is a diagram illustrating an example of an RC oscillator 200 according to an embodiment of the present disclosure. As illustrated in FIG. 2, the RC oscillator 200 according to the present disclosure may include a capacitor sensor (CapSensor) 210, a resister-bank (R-bank) 220 and an inverter 230.

The capacitor sensor 210 may include a fringing field capacitor for generating a fringing field. For example, an inter-digitized electrode type capacitor may be used as the fringing field capacitor. A change within a region of the fringing field (e.g., a change in the concentration of an analyte) formed by the capacitor sensor 210 may derive a change in capacitance of the capacitor sensor 210. A change in capacitance may derive a change in the resonant frequency generated by the RC oscillator 200.

In this case, the system 100 for detecting a concentration of an analyte may measure a change characteristic in an analyte within the fringing field based on a change in the resonant frequency. In this case, as described above, the existing RC oscillator has limitations to the use of a limited frequency. Accordingly, in embodiments of the present disclosure, various resonant frequencies can be generated by variously forming a value of an R component, among the R component and a C component that generate a resonant frequency of the RC oscillator 200, through the R-bank 220. FIG. 2 illustrates an example in which the RC oscillator 200 may selectively output one of multiple resonant frequencies (e.g., one of seven resonant frequencies of seven partial sets except a null set among partial sets of a set {R1, R2, R3}) which may be generated as at least one of three resistance values R1, R2, and R3 is selected by three switches SW1, SW2, and SW3. This is one embodiment. It may be easily understood that various resonant frequencies may be output by implementing an R-bank having more various resistance values and a method of selecting a resistance value may also be variously changed. Furthermore, the R-bank may be implemented to provide a variable resistance value.

The inverter 230 may be used to obtain AC by controlling DC through on/off of the switches according to a basic operation principle, so that consistent oscillation can be formed in a circuit.

For example, a change in the concentration of an analyte within a region of a fringing field may derive a change in capacitance. In this case, a change in capacitance may derive a change in a resonant frequency generated by the RC oscillator 200. The RC oscillator 200 may generate various resonant frequencies by using the R-bank 220. This may mean that various resonant frequencies into which a change in the concentration of the analyte has been incorporated may be generated. Accordingly, the system 100 for detecting a concentration of an analyte may obtain more accurate data of the analyte by obtaining various data into which the concentration of the analyte has been incorporated. This may mean that a more accurate concentration of the analyte can be provided.

Furthermore, the R-bank 220 may play a frequency calibration role capable of incorporating, into a resonant frequency, various elements, such as a race, gender, an age, and an environment which may affect an environment within the body, based on a value of an R component selected by the R-bank 220. In other words, a resonant frequency suitable for an environment within the body of a specific user can be used by selecting a value of the R component suitable for an environment within the body of the specific user by using the R-bank 220.

Figure 3:
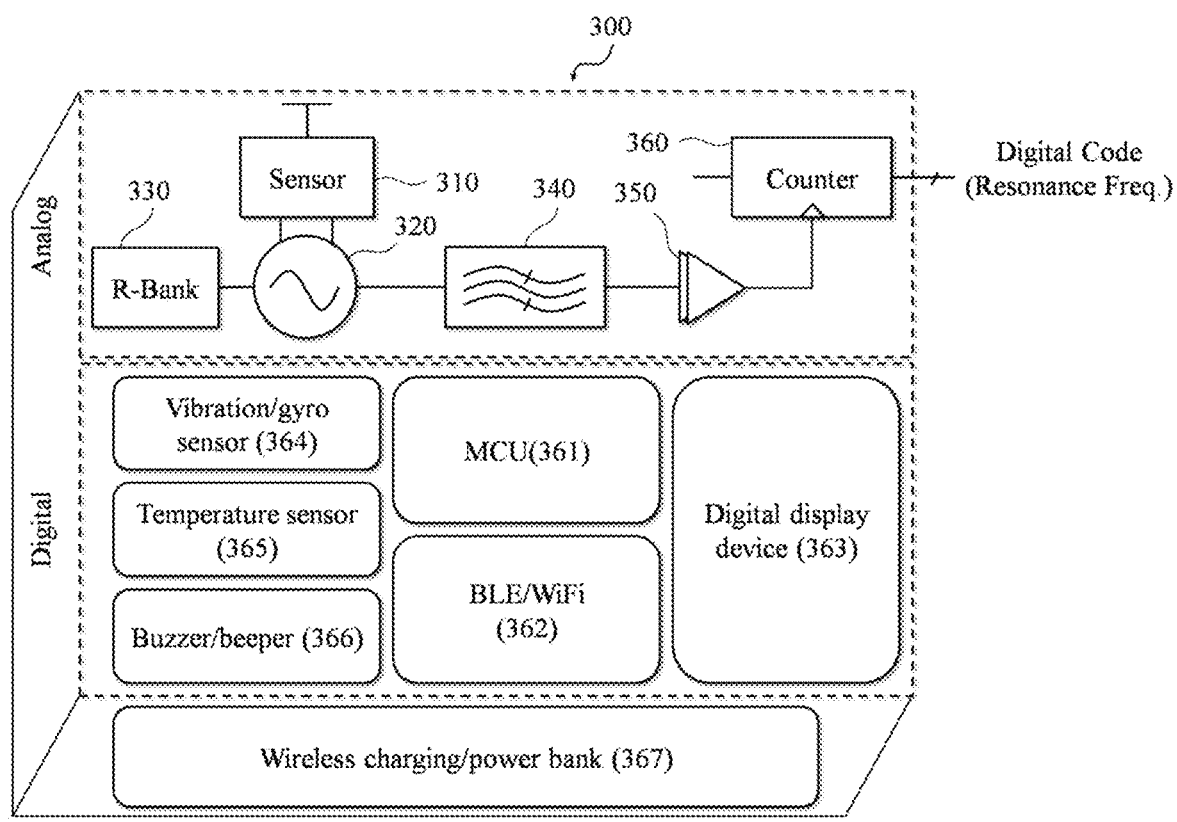
FIG. 3 is a diagram illustrating another example of internal components of a system for detecting a concentration of an analyte according to an embodiment of the present disclosure.

FIG. 3 is a diagram illustrating another example of internal components of a system 300 for detecting a concentration of an analyte according to an embodiment of the present disclosure. The system 300 for detecting a concentration of an analyte according to the present disclosure may include a sensor 310, an oscillator 320, an R-bank 330, a band pass filter (BPF) 340, a buffer 350 and a counter 360 as analog components. Such analog components may be included in the sensor unit 110 described with reference to FIG. 1.

The sensor 310 may be implemented in a form to substantially include a fringing field capacitor included in the oscillator 320. The fringing field capacitor may form a fringing field. As a change in capacitance attributable to a change in an analyte within a region of the fringing field is incorporated into the oscillator 320, a resonant frequency generated by the oscillator 320 may be changed. As described above, the R-bank 330 may be implemented to select one of multiple values of the R component. Accordingly, the oscillator 320 may generate one of various resonant frequencies selectively (or by stages). In this case, the system 300 for detecting a concentration of an analyte may measure a change characteristic in the analyte within the fringing field (e.g., a change in the concentration of the analyte) based on such a change in the resonant frequency. Various data may be collected as a change in the analyte is incorporated into the various resonant frequencies. Accordingly, a change characteristic in the analyte can be more accurately detected using various data.

The BPF 330 is a frequency selection filter that passes a signal having a specific bandwidth. A signal having a frequency out of filter specifications (e.g., a frequency lower than a filter-low cutoff frequency and higher than a filter-high cutoff frequency) may be filtered out at the output of the BPF 330.

The buffer 340 may be used to provide input-output matching between two different circuit components. This is a kind of electric impedance conversion from one circuit to the other circuit, and can prevent a signal loss. For example, the buffer 340 may provide matching between the output of the BPF 330 and the input of the counter 350.

The counter 350 is a circuit for counting the frequency of a scalation signal, and may include a zero-cross detection circuit for an input signal in common.

The system 300 for detecting a concentration of an analyte may include an MCU 361, BLE/WiFi 362, a digital display device 363, a vibration/gyro sensor 364, a temperature sensor 365, and buzzer/beeper 366 as digital components. In this case, the MCU 361 may correspond to or may be included in the processing unit 120 described with reference to FIG. 1. Furthermore, the BLE/WiFi 362 may correspond to or may be included in the communication unit 160 described with reference to FIG. 1. Furthermore, the temperature sensor 365 may correspond to or may be included in the temperature sensor 150 described with reference to FIG. 1. The digital display device 363, the vibration/gyro sensor 364 and the buzzer/beeper 366 may be included in the output unit 170 described with reference to FIG. 1. Although separately described, the gyro sensor may be used to obtain activity information of an object. The gyro sensor is not included in the output unit 170, and may operate as a separate sensor such as the temperature sensor 365, may measure an angular speed of the system 300 for detecting a concentration of an analyte, and may obtain activity information of an object based on the measured angular speed. The obtained activity information may be used to compensate for a concentration of an analyte measured by the sensor unit 110 or to determine the validity of the measured concentration of the analyte. For example, when a change in a value of activity information is equal to or greater than a threshold, the MCU 361 may request the sensor unit 110 to measure a concentration of an analyte again. For another example, when a change in a value of activity information is equal to or greater than the threshold, the MCU 361 may compensate for a measured change characteristic.

Furthermore, the system 300 for detecting a concentration of an analyte may further include a wireless charging/power bank 367. In this case, the "wireless charging" may mean a circuit and antenna for wireless power transmission, and the "power bank" may mean a battery. In other words, the wireless charging/power bank 367 may correspond to or may be included in the power management unit 130 described with reference to FIG. 1.

Figure 4:
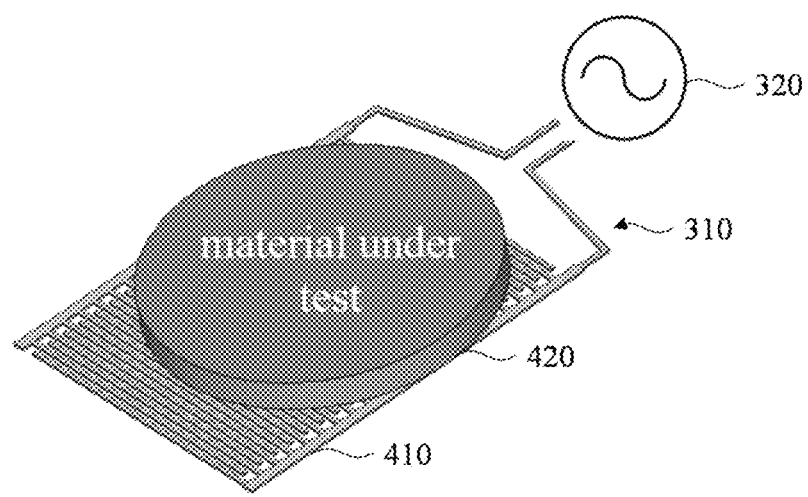
FIG. 4 is a diagram illustrating an example of a sensor according to an embodiment of the present disclosure.

FIG. 4 is a diagram illustrating an example of the sensor according to an embodiment of the present disclosure. FIG. 4 illustrates the sensor 310 and the oscillator 320 described with reference to FIG. 3. As described above, the sensor 310 may be implemented in a form to substantially include a capacitor included in the oscillator 320. In FIG. 4, a sensor pattern 410 may correspond to such a capacitor, and may play a role to generate a fringing field. The sensor 310 may further include a material under test (MUT) unit 420. In this case, the sensor pattern 410 may generate a fringing field. The MUT unit 420 is made of a material having a dielectric constant, and may measure a change in capacitance attributable to a change in permittivity. The MUT unit 420 may be disposed at the center location of the sensor 310 because the sensor 310 commonly operates sensitively at the center location.

Figure 5:
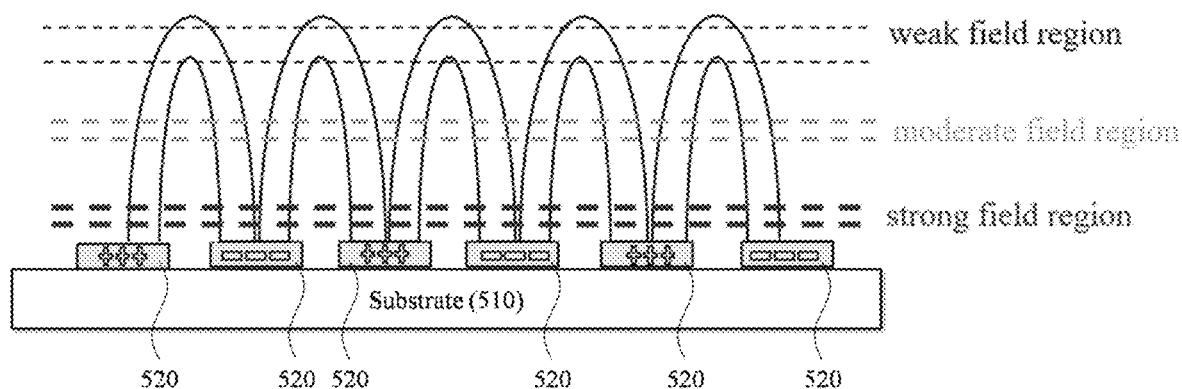
FIG. 5 is a diagram illustrating an example in which a fringing field is generated in an embodiment of the present disclosure.

FIG. 5 is a diagram illustrating an example in which a fringing field is generated in an embodiment of the present disclosure. FIG. 5 illustrates an example in which a fringing field is formed on a substrate 510 as an oscillation signal is applied to metallic sensor traces 520 as the sensor pattern 410 described with reference to FIG. 4. In this case, FIG. 5 illustrates a strong field region, a moderate field region and a weak field region as the fringing field. That is, FIG. 5 illustrates that the intensity of the fringing field is weakened as the distance from the metallic sensor traces 520 becomes distant.

Figure 6:
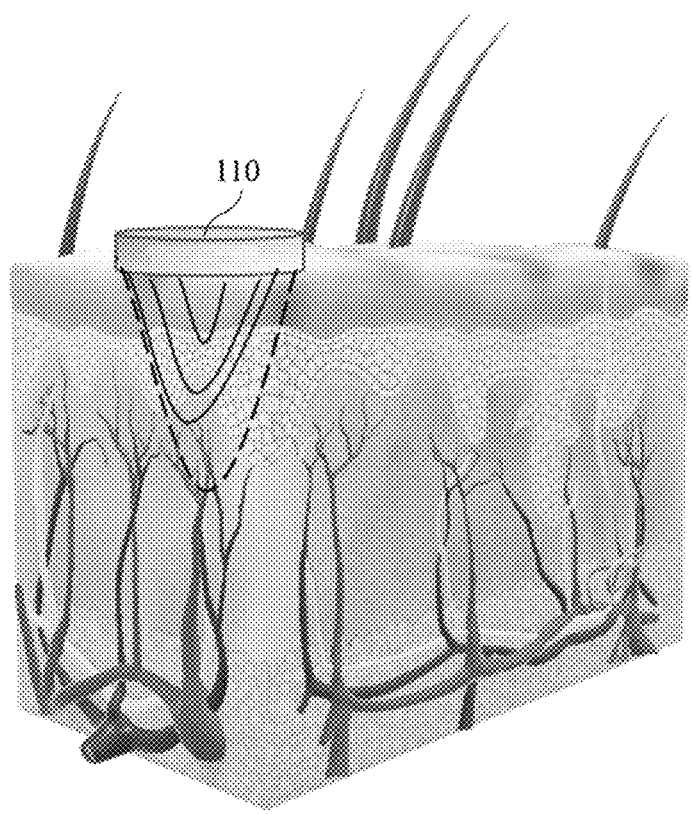
FIG. 6 is a diagram illustrating an example of interactions between a biological tissue, an interstitial fluid (ISF), a blood vessel and a fringing field depending on a penetration depth of the fringing field in an embodiment of the present disclosure.

FIG. 6 is a diagram illustrating an example of interactions between a biological tissue, an interstitial fluid (ISF), a blood vessel, and a fringing field depending on a penetration depth of the fringing field in an embodiment of the present disclosure. As described above, the fringing field from the sensor unit 110 may be used to detect a fine change in a bio permittivity level attributable to the presence of one or more analytes. The sensor unit 110 may incorporate a change in the permittivity level as a change in the resonant frequency.

Figure 7:
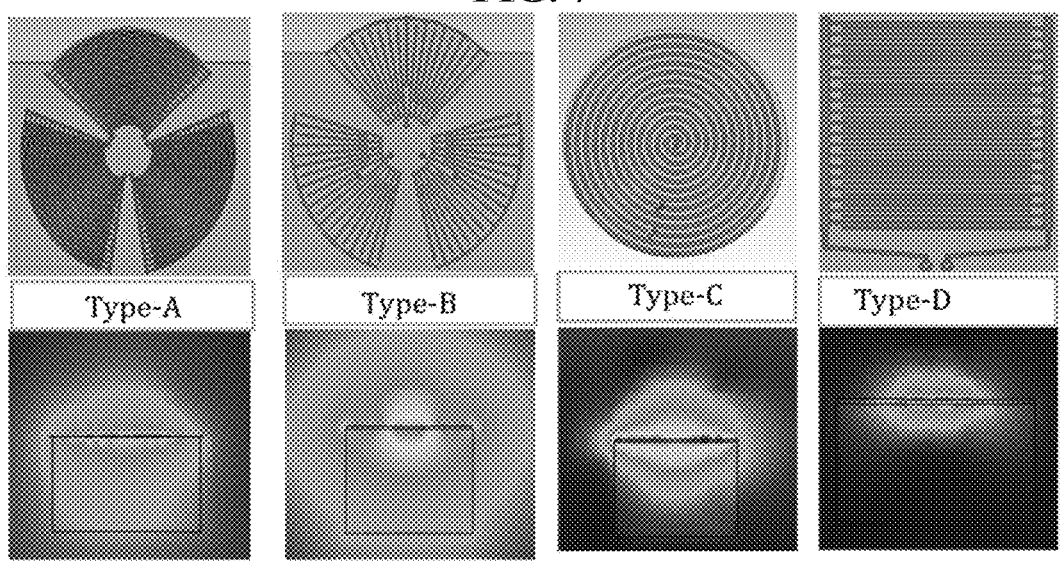
FIG. 7 is an example illustrating the intensity of an electromagnetic field and a degree of skin penetration depending on a sensor pattern in an embodiment of the present disclosure.

FIG. 7 is an example illustrating the intensity of an electromagnetic field and a degree of skin penetration according to a sensor pattern in an embodiment of the present disclosure. FIG. 7 illustrates that the intensity of an electromagnetic field and a degree of skin penetration are different depending on the type of sensor pattern included in the sensor 310. Accordingly, a concentration of various biological analytes can be detected by selectively using a sensor pattern depending on the type of biological analyte (a location within a living body depending on a type) to be measured.

Figure 8:
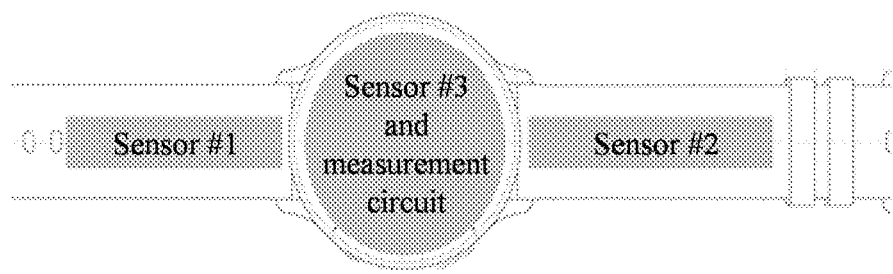
FIG. 8 is a diagram illustrating an example of a system for detecting a concentration of an analyte, which has a wrist watch type, in an embodiment of the present disclosure.

FIG. 8 is a diagram illustrating an example of the system for detecting a concentration of an analyte, which has a wrist watch type, in an embodiment of the present disclosure. The embodiment of FIG. 8 illustrates an example the system for detecting a concentration of an analyte includes a measurement circuit and three sensors. FIG. 8 is an implementation example of the system for detecting a concentration of an analyte, and illustrates an example having a wrist watch type. As described above, the system for detecting a concentration of an analyte may be implemented in an embedded type, and may also be implemented in the form of an implant device inserted into the body of an object. Furthermore, it may be easily understood that the number and locations of sensors may be variously changed, if necessary.

Figure 9:
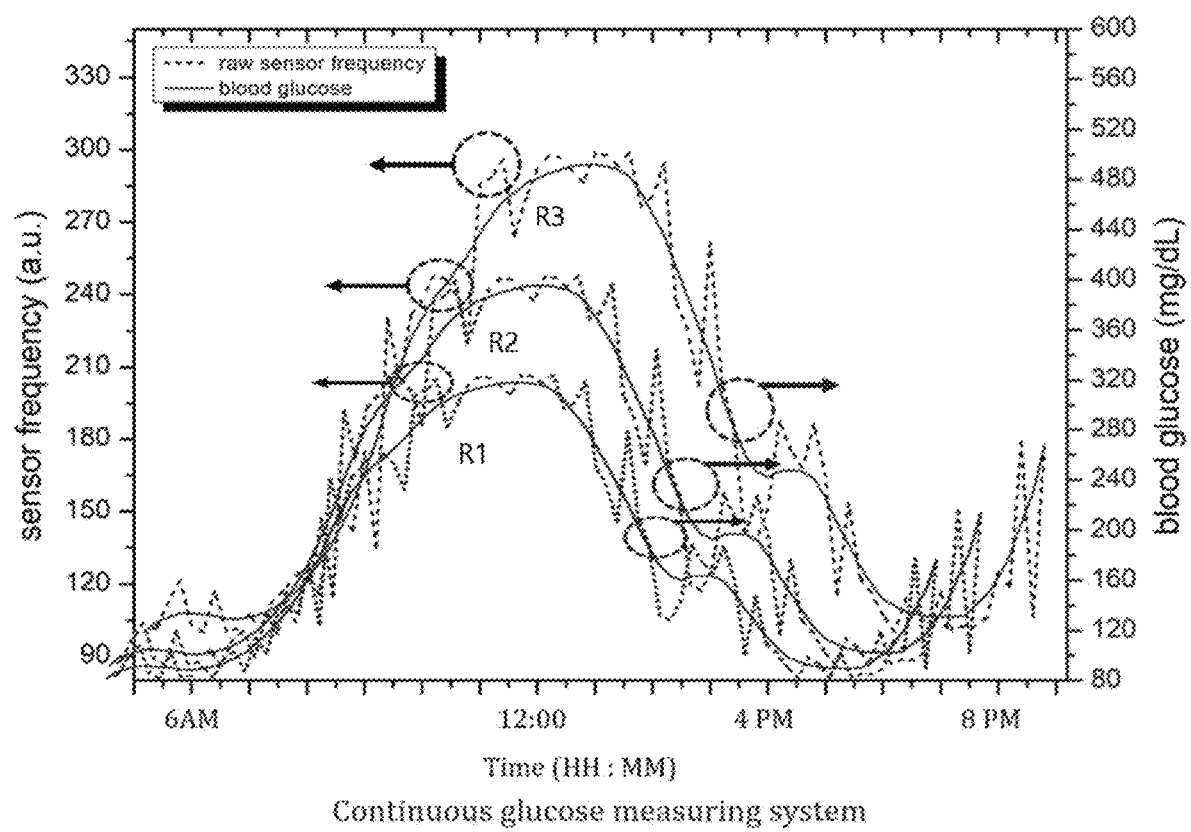
FIG. 9 is a graph illustrating an example of a frequency change attributable to a change in an R value in an embodiment of the present disclosure.

FIG. 9 is a graph illustrating an example of a frequency change attributable to a change in an R value in an embodiment of the present disclosure. The graph illustrates sensor output frequencies according to R values and corresponding blood glucose levels. The sensor may provide a consistent frequency output for an immediate blood glucose level. High frequency noise and a variation may be removed using a tracking, prediction, or averaging filter, if necessary. This may be implemented by both hardware and software algorithms.

Figure 10:
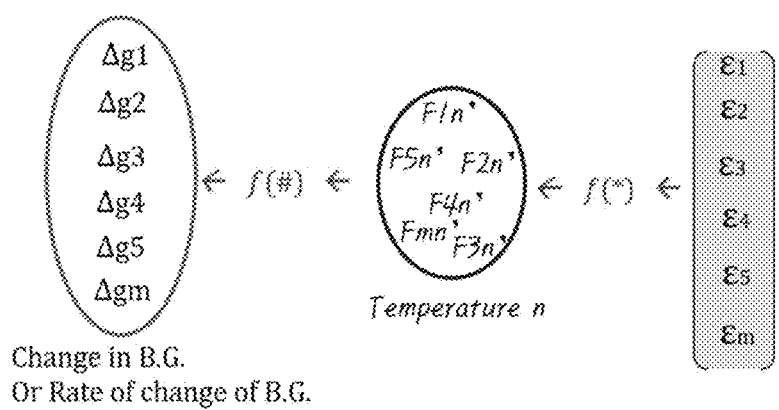
FIG. 10 is a diagram illustrating an example in which a change in an analyte or a rate of change is calibrated based on a temperature in an embodiment of the present disclosure.

FIG. 10 is a diagram illustrating an example in which a change or a rate of change in an analyte is calibrated based on a temperature in an embodiment of the present disclosure. As described above, the sensor 310 may incorporate a change in permittivity into a change in the oscillation frequency. In this case, since the temperature also affects a permittivity level, the system 300 (or the MCU 361) for detecting a concentration of an analyte may calibrate an oscillation frequency of the oscillator attributable to a biological permittivity level through the temperature. The system 300 (or the MCU 361) for detecting a concentration of an analyte may determine a change or a rate of change in an analyte by using a mapping function f(*) and a calibration function f(#). For example, the system 300 (or the MCU 361) for detecting a concentration of an analyte may determine a change or a rate of change in an analyte into which a measured temperature has been incorporated by incorporating the temperature into a change in the resonant frequency or a change characteristic measured with respect to analyte.

FIG. 11 is a flowchart illustrating an example of a method of detecting a concentration of an analyte according to an embodiment of the present disclosure. The method of detecting a concentration of an analyte according to the present disclosure may be performed by the system 100 for detecting a concentration of an analyte, described with reference to FIG. 1, for example.

In step 1110, the system 100 for detecting a concentration of an analyte may generate a fringing field. For example, the fringing field may be generated by the fringing field capacitor of the RC oscillator included in the sensor unit 110.

In step 1120, the system 100 for detecting a concentration of an analyte may generate various resonant frequencies by changing a resistance value of the RC oscillator. For example, the RC oscillator may correspond to the RC oscillator 200 described with reference to FIG. 2 or the oscillator 320 described with reference to FIG. 3. In this case, the system 100 for detecting a concentration of an analyte may select one of various resistance values by using an R-bank (e.g., the R-bank 220 of FIG. 2 or the R-bank 330 of FIG. 3). The RC oscillator may generate a resonant frequency based on the selected resistance value. In this case, the system 100 for detecting a concentration of an analyte may generate various oscillation signals while variously changing the resistance value selected by the R-bank (e.g., selecting the resistance values sequentially or by stages).

In step 1130, the system 100 for detecting a concentration of an analyte may measure a change in a resonant frequency generated by the RC oscillator based on a change in capacitance attributable to a change in an analyte within a region of the fringing field. As described above, a fine change in a bio permittivity level attributable to the presence of one or more analytes in the fringing field may be detected. In this case, the sensor unit 110 may incorporate a change in the permittivity level into a change in the resonant frequency. For example, a change in capacitance may be measured in response to a change in permittivity by using an MUT unit (e.g., the MUT unit 420 of FIG. 4) including a material having a dielectric constant. In this case, in step 1120, when the various resonant frequencies are generated by the R-bank, a change in the permittivity level, in other words, a change in the analyte within a region of the fringing field may be incorporated into the various resonant frequencies. In this case, the system 100 for detecting a concentration of an analyte can obtain various resonant frequencies into which a change in the analyte has been incorporated.

In step 1140, the system 100 for detecting a concentration of an analyte may measure a change characteristic of the analyte within the fringing field based on a change in each of various resonant frequencies. As described above, a change in the permittivity level may be incorporated into a change in the resonant frequency. This may mean that a change in the analyte within a region of the fringing field has been incorporated into a change in the oscillation frequency. The system 100 for detecting a concentration of an analyte can more accurately measure a change characteristic of the analyte based on such various data because a change in the analyte has been incorporated into the various resonant frequencies.

In step 1150, the system 100 for detecting a concentration of an analyte may measure a temperature by using the temperature sensor. The temperature sensor may be implemented to measure a temperature around the system 100 for detecting a concentration of an analyte or the sensor unit 110 included in the system 100 for detecting a concentration of an analyte, for example.

In step 1160, the system 100 for detecting a concentration of an analyte may incorporate the measured temperature into a change in each of the various resonant frequencies or the measured change characteristic. For example, in step 1160, the system 100 for detecting a concentration of an analyte may calculate a change in the resonant frequency into which the temperature has been incorporated or a change or a rate of change in a concentration of the analyte based on the change characteristic.

In some embodiments, the system 100 for detecting a concentration of an analyte may obtain activity information of an object based on an angular speed measured by the gyro sensor, and may compensate for a measured change characteristic based on the obtained activity information of the object. Furthermore, in some embodiments, the system 100 for detecting a concentration of an analyte may determine whether to measure a concentration of an analyte again based on the obtained activity information of the object.

As described above, according to the embodiments of the present disclosure, more accurate data of an analyte can be obtained by obtaining various data into which a concentration of the analyte has been incorporated in a way to form the R-bank capable of variously forming a value of an R component among the R component and a C component which generate a resonant frequency of the RC oscillator, to generate various resonant frequencies based on a value of the R component selected by the R-bank, and to detect and measure a change. Furthermore, various elements, such as a race, gender, an age, and an environment which may change an environment within the body, can be incorporated into a resonant frequency based on a value of the R component selected by the R-bank.

The aforementioned system or device may be implemented as a hardware component, a software component and/or a combination of a hardware component and a software component. For example, the device and components described in the embodiments may be implemented using one or more general-purpose computers or special-purpose computers, for example, a processor, a controller, an arithmetic logic unit (ALU), a digital signal processor, a microcomputer, a field programmable gate array (FPGA), a programmable logic unit (PLU), a microprocessor or any other device capable of executing or responding to an instruction. A processing device may perform an operating system (OS) and one or more software applications executed on the OS. Furthermore, the processing device may access, store, manipulate, process and generate data in response to the execution of software. For convenience of understanding, one processing device has been illustrated as being used, but a person having ordinary knowledge in the art may understand that the processing device may include a plurality of processing components and/or a plurality of types of processing components. For example, the processing device may include a plurality of processors or one processor and one controller. Furthermore, other processing configurations, such as a parallel processor, are also possible.

Software may include a computer program, a code, an instruction or a combination of one or more of them, and may configure a processor so that it operates as desired or may instruct processors independently or collectively. Software and/or data may be embodied in any type of a machine, component, physical device, virtual equipment, or computer storage medium or device so as to be interpreted by the processor or to provide an instruction or data to the processor. The software may be distributed to computer systems connected over a network and may be stored or executed in a distributed manner. The software and data may be stored in one or more computer-readable recording media.

The method according to the embodiment may be implemented in the form of a program instruction executable by various computer means and stored in a computer-readable recording medium. The computer-readable recording medium may include a program instruction, a data file, and a data structure alone or in combination. The program instructions stored in the medium may be specially designed and constructed for the present disclosure, or may be known and available to those skilled in the field of computer software. Examples of the computer-readable storage medium include magnetic media such as a hard disk, a floppy disk and a magnetic tape, optical media such as a CD-ROM and a DVD, magneto-optical media such as a floptical disk, and hardware devices specially configured to store and execute program instructions such as a ROM, a RAM, and a flash memory. Examples of the program instructions include not only machine language code that is constructed by a compiler but also high-level language code that can be executed by a computer using an interpreter or the like.

As described above, although the embodiments have been described in connection with the limited embodiments and the drawings, those skilled in the art may modify and change the embodiments in various ways from the description. For example, proper results may be achieved although the aforementioned descriptions are performed in order different from that of the described method and/or the aforementioned components, such as the system, configuration, device, and circuit, are coupled or combined in a form different from that of the described method or replaced or substituted with other components or equivalents.

Accordingly, other implementations, other embodiments, and the equivalents of the claims fall within the scope of the claims.

The embodiments of the invention in which an exclusive property or privilege is claimed are defined as follows:

1. A method of detecting a concentration of an analyte, comprising:
generating various resonant frequencies by changing a resistance value of a resistor-capacitor (RC) oscillator;
measuring a change in each of the various resonant frequencies generated by the RC oscillator based on a change in capacitance attributable to a change in an analyte within a region of a fringing field formed by the various resonant frequencies; and
measuring a change characteristic of the analyte within the fringing field based on the change in each of the various resonant frequencies.

2. The method of claim 1, wherein:
generating the resonant frequency comprises changing the resistance value of the RC oscillator through a resister-bank (R-bank) included in the RC oscillator, and
the R-bank is implemented to selectively use one of multiple resistance values or to provide a variable resistance value.

3. The method of claim 1, wherein generating the fringing field comprises generating the fringing field by using a fringing field capacitor included in the RC oscillator.

4. The method of claim 1, wherein the change in capacitance is measured based on a change in permittivity by using a material under test (MUT) unit comprising a material having a dielectric constant.

5. The method of claim 1, further comprising:
measuring a temperature by using a temperature sensor; and
incorporating the measured temperature into the change in each of the various resonant frequencies or the measured change characteristic of analyte.

6. The method of claim 1, further comprising:
obtaining activity information of an object based on an angular speed measured by a gyro sensor; and
compensating for the measured change characteristic of analyte based on the obtained activity information of the object.

7. A system for detecting a concentration of an analyte, comprising:
a sensor unit; and
a processing unit,
wherein the sensor unit is configured to:
generate various resonant frequencies by changing a resistance value of a resistor-capacitor (RC) oscillator, and
generate various resonant frequencies into each of which a change in capacitance attributable to a change in an analyte within a region of a fringing field has been incorporated formed by the various resonant frequencies, and
the processing unit is configured to measure a change characteristic of the analyte within the fringing field based on the change in each of the various resonant frequencies into each of which the change in the capacitance has been incorporated.

8. The system of claim 7, wherein the sensor unit comprises the RC oscillator configured to generate the fringing field and the various resonant frequencies.

9. The system of claim 8, wherein the RC oscillator comprises:
a fringing field capacitor configured to generate the fringing field; and
a resister-bank (R-bank) implemented to selectively use one of multiple resistance values or to provide a variable resistance value.

10. The system of claim 9, wherein the sensor unit changes the resistance value of the RC oscillator by using the R-bank included in the RC oscillator.

11. The system of claim 8, wherein the fringing field capacitor comprises:
a sensor pattern for generating the fringing field; and a material under test (MUT) unit comprising a material having a dielectric constant and configured to measure a change in capacitance attributable to a change in permittivity.

12. The system of claim 8, wherein the sensor unit further comprises:
    a band pass filter (BPF) configured to filter out a signal having a frequency out of filter specifications from an output signal of the RC oscillator;
    a buffer configured to provide matching between an output of the BPF and an input of a counter in order to prevent a signal loss; and
    the counter configured to count a frequency of a scalation signal as a zero-cross detection circuit for a signal output by the buffer.

13. The system of claim 7, further comprising a temperature sensor configured to measure a temperature around the sensor unit,
    wherein the processing unit incorporates the measured temperature into the change in each of the various resonant frequencies or the measured change characteristic of analyte.

14. The system of claim 7, further comprising:
    a communication unit for communication with another external device;
    an output unit configured to output at least one of a concentration of the analyte calculated based on the change characteristic of the analyte and a warning based on the concentration of the analyte; and
    a power management unit configured to provide power to at least one of the sensor unit, the processing unit, the communication unit and the output unit,
    wherein the processing unit controls an operation of at least one of the sensor unit, the communication unit, the output unit and the power management unit.

15. The system of claim 14, wherein:
    the power management unit comprises at least one of a battery and a component for wireless power transfer, and
    the component comprises a circuit and antenna for wireless power transfer.

16. The system of claim 7, further comprising a noise removal unit configured to remove noise from a signal output by the sensor unit.

17. The system of claim 7, further comprising a gyro sensor configured to measure an angular speed of the system for detecting a concentration of an analyte,
    wherein the measured change characteristic of analyte is compensated for based on activity information of an object based on the angular speed.

* * * * *